United States Patent [19]

Metz-Stavenhagen

[11] Patent Number: 6,090,110
[45] Date of Patent: *Jul. 18, 2000

[54] APPARATUS FOR BRACING VERTEBRAE

[75] Inventor: Peter Metz-Stavenhagen, Bad Wildungen, Germany

[73] Assignee: Howmedica GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/839,540

[22] Filed: Apr. 14, 1997

Related U.S. Application Data

[63] Continuation of application No. 08/384,639, Feb. 6, 1995, abandoned, which is a continuation of application No. 08/025,196, Mar. 2, 1993, abandoned.

[30] Foreign Application Priority Data

Mar. 2, 1992 [DE] Germany .................. 92 02 745 U

[51] Int. Cl.⁷ ................... A61B 17/18; A61B 17/56; A61F 5/00
[52] U.S. Cl. ................ 606/61; 606/72; 606/73; 623/17
[58] Field of Search ................ 606/60, 61, 72, 606/73; 623/17

[56] References Cited

U.S. PATENT DOCUMENTS

| | | | |
|---|---|---|---|
| 4,047,524 | 9/1977 | Hall | 128/69 |
| 4,383,438 | 5/1983 | Eaton | 73/61.2 |
| 4,854,304 | 8/1989 | Zielke | 128/69 |
| 4,987,892 | 1/1991 | Krag et al. | 606/60 |
| 5,042,982 | 8/1991 | Harms et al. | 606/60 |
| 5,129,388 | 7/1992 | Vignaud | 606/61 |
| 5,176,680 | 1/1993 | Vignaud et al. | 606/61 |
| 5,207,678 | 5/1993 | Harms et al. | 606/61 |

FOREIGN PATENT DOCUMENTS

| | | | |
|---|---|---|---|
| 0443892B1 | 8/1991 | European Pat. Off. | |
| 2649042 | 1/1978 | Germany | 606/60 |
| 2131300 | of 0000 | United Kingdom | |
| 9101691 | 2/1991 | WIPO | |
| 9203100 | 5/1992 | WIPO | 606/61 |

*Primary Examiner*—Linda C. M. Dvorak
*Assistant Examiner*—Sonya Hans-Ogugua
*Attorney, Agent, or Firm*—Lerner, David, Littenberg, Krumholz & Mentlik, LLP

[57] ABSTRACT

An apparatus for bracing a plurality of vertebrae of the human spine has at least two pedicle screws, each having an annular head with an opening therewithin and including a slot therewithin. Each slot extends into the corresponding opening and includes internal threaded portions. A securing screw to be screwed in each slot is provided. A relatively stiff threaded rod is also provided and is to be inserted into the opening in the head of each of the pedicle screws and to be secured by the securing screws. Adjusting nuts are screwed on the rod and at least one cooperates with each head.

20 Claims, 3 Drawing Sheets

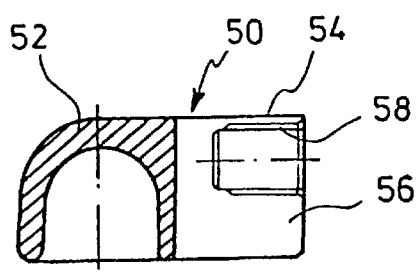
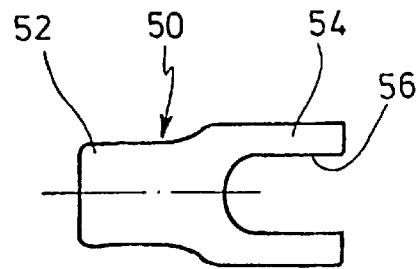
FIG. 11    FIG. 12
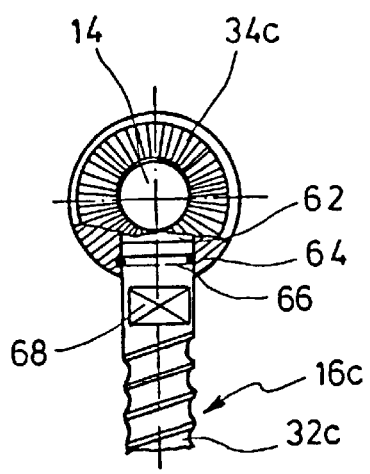
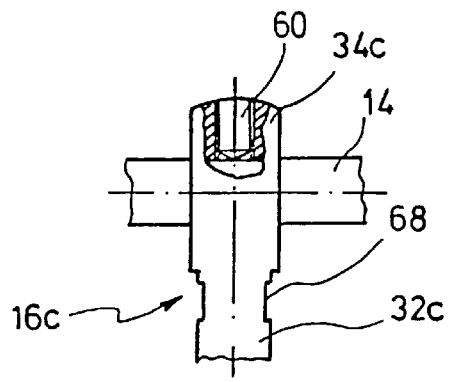
FIG. 13    FIG. 14
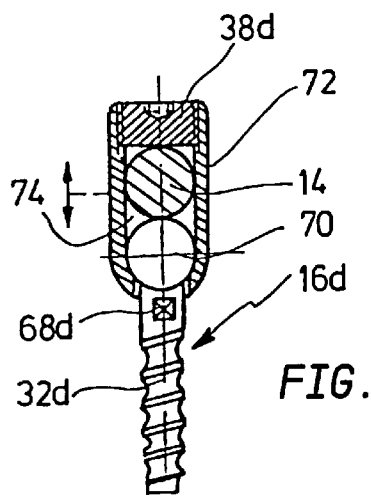
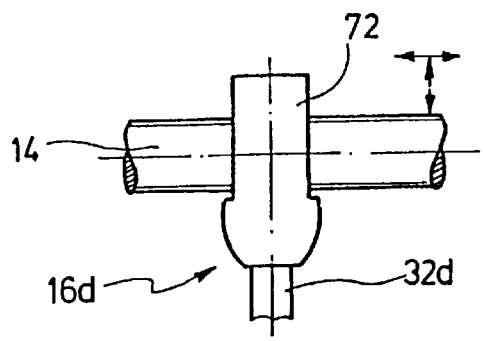
FIG. 15    FIG. 16

APPARATUS FOR BRACING VERTEBRAE

This is a continuation of application Ser. No. 08/384,639, filed on Feb. 6, 1995abandoned Apr. 14, 1999 which is a continuation of application Ser. No. 08/025,196, filed on Mar. 2, 1993, abandoned Feb. 6, 1995.

The present invention relates to an apparatus for bracing a plurality of vertebrae of the human spine.

Known supporting means operate with so-called lamina hooks which are disposed on a threaded rod. A compressing means is disclosed in British patent 2 131 300. A distracting means is disclosed in U.S. Pat. No. 4,383,438. The threaded rod bridges a plurality of vertebrae and is not suited to act on vertebrae which are disposed between the lamina hooks. The thread of the rod is used to fix the lamina hooks. Before using the supporting means a distraction or, respectively, compression has to be provided by means of an additional device.

German 90 06 646 U1 discloses an apparatus in which a lamina hook is replaced by a clamp-shaped holding member having a pair of legs of which one can be bent with respect to the other. Thereby the giapophysis of the vertebrae may be used as anchoring points for the compressing and distracting apparatus.

German 88 02 112 U1 teaches a supporting device for the human spine, according to which the so-called pedicle screws are screwed into the pedicle body of the vertebrae. The pedicle screws cooperate with tensioning means which bridge across one or more vertebrae to introduce forces between the vertebrae. The known device affords a primary stabilization of the vertebrae with respect to all degrees of freedom. However, when a number of vertebrae of a non-traumatic spine for example, are to be repositioned, separate means necessary to perform the repositioning before the known supporting device may be effectively used.

WO 91/01691 discloses an apparatus for bracing vertebrae of the human spine, comprising pedicle screws having slotted heads to receive a rod. The legs of the slotted screw heads include an outer thread on which a nut is screwed which contacts the rod to fix a predetermined position.

EP 0 443 892 discloses a similar device comprising a pedicle screw, the slotted head thereof including internal threaded portions for receiving a fixing screw which is brought into engagement with a serrated or similarly roughened rod to fix the relative position of the rod and the individual pedicle screw. A ring disposed around the head of a pedicle screw is provided so that the legs of the screw head do not spread apart while fixing the rod, as otherwise the engagement between the fixing screw and the screw head may be lost. A similar apparatus is disclosed in WO 90/09156.

Again, the devices last mentioned require separate means for repositioning, thus being suited to maintain a repositioned condition, but not suited to perform repositioning.

It is an object of the present invention to provide an apparatus which is suited to reposition the vertebrae of the human spine as well as to support the vertebrae in the repositioned position thereafter.

The objects are solved by the apparatus of the invention.

SUMMARY OF THE INVENTION

According to the invention, the apparatus uses a threaded rod (i.e., a distracting rod) in combination with lamina hooks. The thread of the rod, however, is not only used to fix the pedicle screws, but further is used to reposition the vertebrae in that an adjusting nut sitting on the threaded rod is turned with respect to the head of the pedicle screw and thus the vertebra has obtained the desired position. By means of the apparatus according to the invention a spine portion is not only distracted or compressed, but individual vertebrae can be effectively positioned with respect to each other. To this end the threaded rod is designed to be relatively stiff and has a diameter between 7 to 8 mm, for example. On the other hand the rod must be bent to be implanted close to the spine along a bent spine portion. This is facilitated by the design of the pedicle screw heads having slots for receiving the threaded rod. To hold the rod in the slot, a securing screw is provided. Whereas the screw in the pedicle screw head according to EP 0 443 892, for example, axially fixes the rod, the securing screw of the present invention is merely used to prevent a deflection of the rod out of the receiving slot.

After resetting, the adjusting nut must be fixed on the threaded rod. This can be obtained by means of a suitable counter-nut. Still further, it is possible, to provide the adjusting nut and the front faces of the pedicle screw head with a rotary safety means in form of a toothing or another irregularity cooperating in a clamping fashion. In both cases the nuts are merely fixed by a frictional force. According to a further embodiment of the invention, however, the head of the pedicle screw has a width smaller than the diameter of the securing screw, whereas at least one front face of the adjusting nut has a recess cooperating with the securing screw. Preferably, the adjusting nut includes a plurality of peripherally spaced indentations, wherein the final rotary position of the nut is such that the securing screw cooperates with the indentation. This affords a positive locking of the adjusting nut resulting in a precise rotary locking which cannot be loosened.

The pedicle screws must take up relatively large forces. There is the danger that a pedicle screw may break out of the bone, primarily when the available bony substance does not provide a sufficiently rigid seat in the vertebra. According to an embodiment of the invention, a mounting strap is attached to the shaft of the pedicle screw laterally extending therefrom, which strap includes an opening for receiving a spongiose screw. The strap has, for example, a pair of openings, wherein one opening receives the shaft of the pedicle screw, while the other opening disposed at the other end of the strap, for example, receives a spongiose screw which is screwed into the vertebra. In this manner, the pedicle screw is laterally stabilized and can receive substantial forces. According to an alternate embodiment of the invention, a mounting strap may be provided to the shaft of the pedicle screw extending therefrom, which strap has a blade or the like to be mounted in the vertebra. The blade is preferably integral with the strap. The blade is beaten into the vertebra wherein the strap may additionally include a hole for receiving a spongiose screw which is screwed into the vertebra. In some cases, a vertebra is displaced with respect to the adjacent vertebra. When the pedicle screw is completely screwed in, it cannot be connected any more with the threaded rod. To accomplish a connection, the pedicle screw is partly screwed into the vertebra bone. According to an embodiment of the invention, the head of the pedicle screw is then rotatably mounted on the screw shaft so that by rotating the shaft the vertebra can be pulled up to the threaded rod for resetting. Preferably the shaft includes tool engaging faces adjacent the head to rotate the shaft of the screw in the desired manner.

In case of very specially displaced individual vertebrae, not even the features referred to above are suffient. According to a further embodiment of the invention, the upper end of the pedicle screw shaft is ball-shaped, while the pedicle screw head is defined by a ball-engaging cage including a slot for the rod. The cage can be arbitrarily positioned with respect to the shaft of the screw, but can exert a tensioning force to the screw shaft when being screwed into the vertebra. According to both embodiments just referred to, the threaded rod is inserted through a slot of the pedicle screw head, wherein a securing screw referred to several times prevents the rod from sliding out of the slot. Alternatively a closed passage may be provided in the head of the pedicle screw as it is known per se.

Instead of or in addition to the pedicle screw the apparatus of the present invention provides a hook cooperating with a lamina of a vertebra. Those lamina hooks are generally known. According to the invention, however, the lamina hook is provided with a slotted receiving portion to insert the threaded rod. The slot has threaded portions again to secure the rod in the receiving slot.

DESCRIPTION OF THE PREFERRED EMBODIMENTS

Preferred embodiments of the invention will now be described by way of example with reference to the accompanying drawing.

Figure 2:
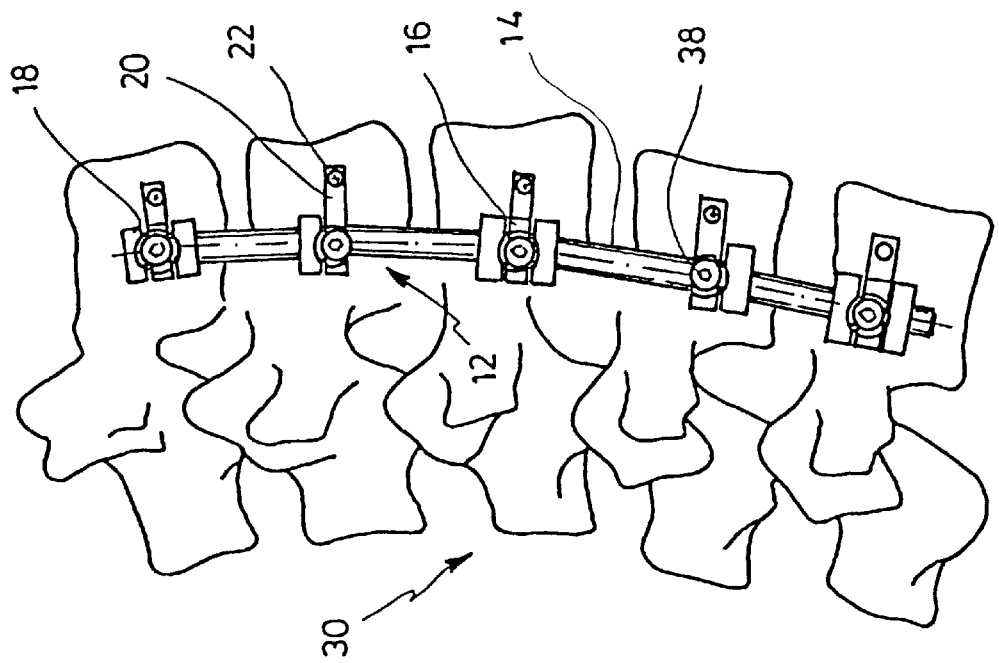
Figure 1:
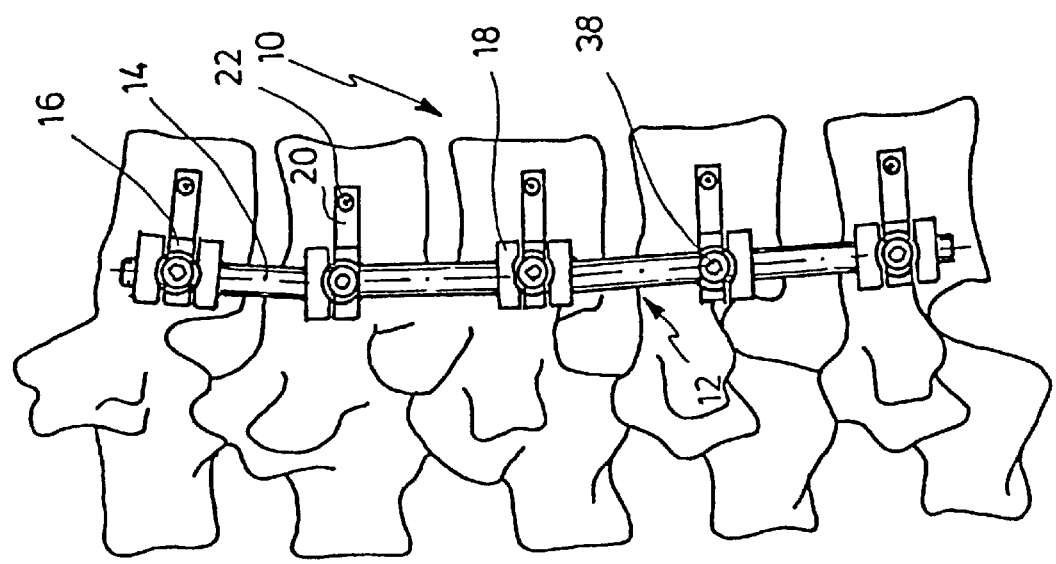
Figure 3:
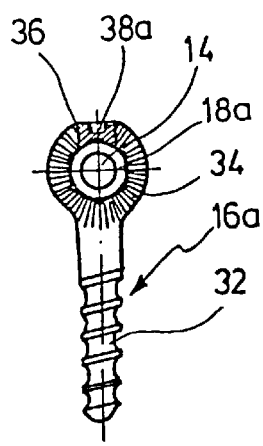
Figure 4:
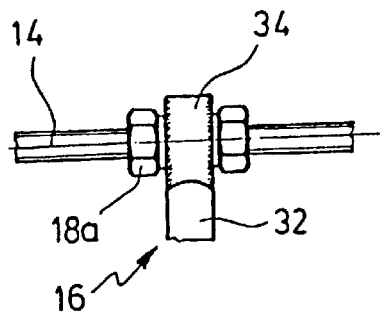
Figure 7:
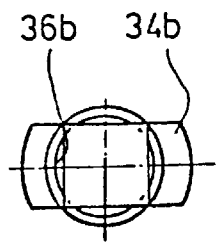
Figure 5:
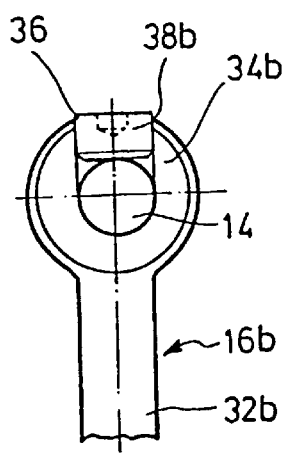
Figure 6:
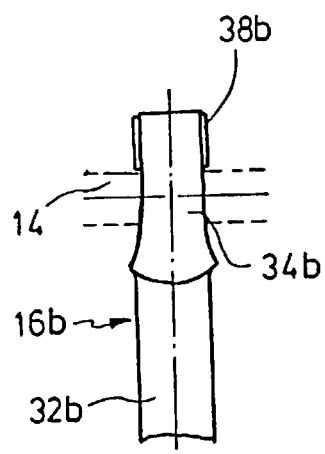
Figure 8:
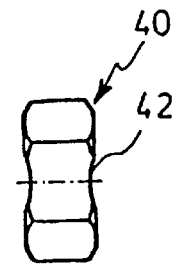
Figure 9:
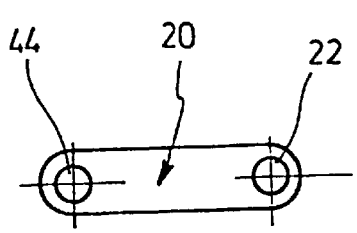
Figure 10A:
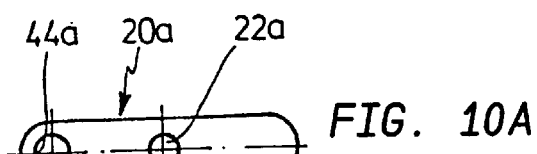
Figure 10B:

FIG. 1 schematically shows an apparatus according to the invention to be used as a distracting system, FIG. 2 schematically shows an apparatus according to the invention used as a compressing system, FIG. 3 shows a pedicle screw for the apparatuses according to FIGS. 1 and 2, FIG. 4 shows the pedicle screw of FIG. 3 cooperating with a threaded rod, FIG. 5 schematically shows a side view of a further embodiment of a pedicle screw for the apparatuses of FIGS. 1 and 2, FIG. 6 shows a side view of the pedicle screw of FIG. 5 rotated about 90°, FIG. 7 shows a plan view of the pedicle screw of FIG. 5, FIG. 8 shows a side view of an adjusting nut of the apparatus of FIGS. 1 and 2, FIG. 9 shows a stabilizing strap for the apparatus of FIGS. 1 and 2, FIG. 10 shows a further embodiment of a stabilizing strap of the apparatus of FIGS. 1 and 2, FIG. 11 shows a section of a lamina hook for the apparatus of FIGS. 1 and 2, FIG. 12 shows a plan view of the hook of FIG. 11, FIG. 13 shows a side view of a further embodiment of a pedicle screw for an apparatus according to the invention, FIG. 14 shows a side view of the pedicle screw of FIG. 13 turned about 90°, FIG. 15 shows a side view partly in section of a further embodiment of a pedicle screw for an apparatus according to the invention and FIG. 16 shows a side view of the pedicle screw of FIG. 15 turned around 90°.

FIG. 1 shows a bent spine portion 10 wherein the individual vertebrae are to be distracted by means of a distracting system 12. The system comprises a relatively stiff threaded rod 14 having a diameter of 6 to 9 mm, preferably 7 to 8 mm. It cooperates with an individual pedicle screw 16 screwed in the vertebrae. Details of the screws are shown in the following figures. The threaded rod 14 is received in slots of the pedicle screw heads 16 and a plurality of adjusting nuts 18 is disposed on the rod 14, at least one nut each for a pedicle screw 16. Stabilizing latches 20 cooperate with the pedicle screws, which latches include a hole 22 in a distance from the pedicle screw to receive a spongiose screw screwed in the vertebra. By means of the adjusting nut 18 a pedicle screw screwed in the vertebra may be displaced relative to the rod 14 and thus with respect to the vertebra receiving the screw. By means of the adjusting nuts 18 the vertebrae of the portion 10 may be thus adjusted to accomplish a distraction.

The spine portion 30 shown in FIG. 2 comprises a compressing means including components identical with those shown in the system 12 so that identical components carry identical reference numerals. To reduce the bending of the spine portion 30 a tension force must be exerted on the vertebras to straighten the bent threaded rod 14. This is accomplished by adjusting the individual pedicle screws 16 as described in FIG. 1. In the following the components of the system referred to are described in more detail. FIG. 3 shows a pedicle screw 16a having a shaft 32 and an annular head 34. The head 34 includes a slot 36 in which the rod 14 is inserted. A securing screw 38a cooperating with threaded portions in the slot 36 holds the threaded rod 14 in the slot 36. FIG. 4 shows adjusting nuts 18a located on either side of the head 34 to displace the screw 16a along the rod 14.

In the embodiment of FIGS. 5 and 6 the pedicle screw 16b has a relatively narrow head 34b so that the securing screw 38b laterally projects. This is shown by the dashed line in FIG. 7. When an adjusting nut 40 according to FIG. 8 is used, which nut is provided with indentations 42 on the opposite front faces thereof, the nut 40 can be secured to the rod 14 when an indentation 42 of the screw 38b cooperates with the adjusting nut 38b.

FIG. 9 shows a mounting strap or latch or flap. The plate-shaped strap 20 includes a first hole 44 receiving the shaft of a pedicle screw. A second hole 22 receives a spongiose screw as mentioned before.

FIG. 10 shows an alternate embodiment 20a of a stabilizing strap or flap or latch, again comprising a hole 44a for a pedicle screw and a hole 22a located substantially in the center for receiving a spongiose screw. FIG. 10 further shows a blade 46 integrally shaped on the end opposite the hole 44a which blade is driven home in the vertebra.

FIGS. 11 and 12 show a lamina hook 50 comprising a hook portion 52 and a receiving portion 54 including a slot 56. The slot 56 receives a threaded rod such as the rod 14 shown in FIGS. 1 and 2. Threaded portions as indicated at 58 in FIG. 11 are provided inside the slot 56 to receive a securing screw (not shown) to hold the rod in the slot 56. The position of the rod in the slot 56 is determined by the position of the securing screw (not shown), wherein a relative position between the hook 50 and the rod is possible to a limited extent.

FIGS. 13 and 14 show a pedicle screw 16c comprising a shaft 32c and an annularly closed head 34b through which a rod 14 extends. A fixing screw 60 in the head 34b is used to fix the threaded rod 14. However, adjusting nuts may be used as mentioned before. According to the embodiment of FIGS. 13, 14 the shaft 32c is rotatably mounted in the head 34b. Accordingly, a circular blind bore 62 holds a ring 64 cooperating with an annular groove 66 in the shaft 32. Tool faces 68 facilitate a rotation of the shaft 32c relative to the head 34c when it fixedly sits on the rod 14 for example. It should be understood that the head 34c may provide a slot as shown in FIGS. 3 to 7 for example.

In the embodiment of FIGS. 15 and 16 a pedicle screw 16d is provided comprising a shaft 32d which upper end is formed as a ball. A cage 72 cooperates with the ball, the cage further having an opening passage 74 to receive a threaded rod 14. Furthermore, the cage 72 has threaded portions to receive a securing screw 38c. This allows to rotate the shaft 32, wherein tool faces 68d are provided. Furthermore, the shaft 32d may be pivoted relative to the cage 72 in a limited angle.

I claim:

1. An apparatus for bracing a plurality of vertebrae, the apparatus comprising at least two pedicle screw assemblies having an integral upper end terminating in an elongated segment having at least two parallel walls facing one another with an opening therebetween, the opening defined at least in part by flat inner surfaces of the parallel walls, a plate shaped member having a first hole for receiving a shaft of the pedicle screw and a second hole for receiving a spongiose screw and a threaded rod extending between said pedicle screws including a nut for making contact with said pedicle screws.

2. The apparatus of claim 1 wherein the at least two pedicle screw assemblies further contain a threaded slot at the top of the upper end.

3. The apparatus of claim 2 wherein the threaded slot contains internal threads.

4. The apparatus of claim 3 wherein the at least two pedicle screw assemblies have a securing screw screwed into the slot.

5. The apparatus of claim 1 wherein the at least two parallel walls are congruent in length and the height of the at least two parallel walls is greater than the width of the elongated segment.

6. An apparatus for bracing a plurality of vertebrae, the apparatus comprising:

(a) at least two pedicle screw assemblies having an integral upper end terminating in an elongated segment having at least two parallel walls facing one another with an opening therebetween, the opening defined at least in part by flat inner surfaces of the parallel walls;

(b) a rod inserted into and between the openings of the pedicle screw assemblies;

(c) a nut disposed about the rod and making contact with at least one of the pedicle screw assemblies; and (d) a plate shaped member having a first hole for receiving a shaft of the pedicle screw and a second hole for receiving a spongiose screw.

7. The apparatus of claim 6 wherein the at least two pedicle screw assemblies further contain a threaded slot at the top of the upper end.

8. The apparatus of claim 7 wherein the threaded slot contains internal threads.

9. The apparatus of claim 8 wherein the at least two pedicle screw assemblies have a securing screw screwed into the slot.

10. The apparatus of claim 6 wherein the at least two parallel walls are congruent in length and the height of the at least two parallel walls is greater than the width of the elongated segment.

11. An apparatus for bracing a plurality of vertebrae, the apparatus comprising:

(a) at least two pedicle screw assemblies having an integral upper end terminating in an elongated segment having at least two parallel walls facing one another with an opening therebetween, the opening defined at least in part by flat inner surfaces of the parallel walls;

(b) a substantially flat reinforcing member disposed about the pedicle screw and having a hole adapted to receive a spongiose screw;

(c) a rod inserted into and between the openings of the pedicle screw assemblies; and (d) a nut disposed about the rod and making contact with at least one of the pedicle screw assemblies.

12. The apparatus of claim 11 wherein the rod is threaded and has a diameter of between 6 and 9 mm.

13. The apparatus of claim 12 wherein the threaded rod has a diameter of between 7 and 8 mm.

14. The apparatus of claim 11 wherein the at least two parallel walls are congruent in length and the height of the at least two parallel walls is greater than the width of the elongated segment.

15. The apparatus of claim 11 wherein the at least two pedicle screw assemblies further contain a threaded slot at the top of the upper end.

16. The apparatus of claim 15 wherein the threaded slot contains internal threads.

17. The apparatus of claim 16 wherein the at least two pedicle screw assemblies have a securing screw screwed into the slot.

18. The apparatus of claim 17 wherein the nut has a recess provided on at least one front face.

19. The apparatus of claim 11 wherein the at least two pedicle screw assemblies include a solid ball disposed partially within the two parallel walls.

20. The apparatus of claim 11 wherein said reinforcing member includes a blade integrally formed on an end thereof for insertion into the vertebra.

* * * * *

UNITED STATES PATENT AND TRADEMARK OFFICE
CERTIFICATE OF CORRECTION

PATENT NO.   :   6,090,110
DATED        :   July 18, 2000
INVENTOR(S)  :   Metz-Stavenhagen It is certified that error appears in the above-identified patent and that said Letters Patent is hereby corrected as shown below:

Column 4, line 16, "vertebras" should read -- vertebrae --.
Column 4, line 19, begin a new paragraph with "FIG. 3".
Column 5, line 2, "an opening" should read -- a --.

Signed and Sealed this

Seventeenth Day of April, 2001

Attest:

NICHOLAS P. GODICI

Attesting Officer

Acting Director of the United States Patent and Trademark Office